United States Patent
Tenengauzer et al.

(10) Patent No.: US 6,764,997 B2
(45) Date of Patent: Jul. 20, 2004

(54) STABILIZED AZITHROMYCIN COMPOSITIONS

(75) Inventors: Ruth Tenengauzer, Hod Hasharon (IL); Joseph Schwarz, Toronto (CA); Julia Hrakovsky, Rosh-H-Ayin (IL); Tania Lessen, Toronto (CA); Lev Khondo, Toronto (CA); Mathi Mathivanan, Markham (CA); Claude Singer, Kfar Saba (IL); Michael Pesachovich, Ramat Gan (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/274,097

(22) Filed: Oct. 18, 2002

(65) Prior Publication Data

US 2003/0176369 A1 Sep. 18, 2003

Related U.S. Application Data

(60) Provisional application No. 60/336,346, filed on Oct. 18, 2001, provisional application No. 60/331,931, filed on Nov. 21, 2001, and provisional application No. 60/341,295, filed on Dec. 17, 2001.

(51) Int. Cl.[7] ............................................... A61K 31/70
(52) U.S. Cl. .......................................... 514/29; 536/7.4
(58) Field of Search ............................... 536/7.4; 514/29

(56) References Cited

U.S. PATENT DOCUMENTS

| 5,605,889 A | 2/1997 | Curatolo et al. |
| 5,872,104 A | 2/1999 | Vermeulen et al. |
| 6,239,112 B1 | 5/2001 | Macy et al. |
| 6,239,113 B1 * | 5/2001 | Dawson et al. ............... 514/29 |
| 6,365,574 B2 | 4/2002 | Singer et al. |

FOREIGN PATENT DOCUMENTS

WO    WO 99/58541    11/1999

* cited by examiner

*Primary Examiner*—Elli Peselev
(74) *Attorney, Agent, or Firm*—Kenyon & Kenyon

(57) ABSTRACT

Compositions and methods of stabilizing azithromycin compositions are described. Stabilized azithromycin compositions comprise an intimate admixture of azithromycin and a stabilizing-effective amount of an antioxidant to improve the resistance of the azithromycin to degradation. Coprecipitation or co-milling of azithromycin and an antioxidant are particularly preferred means of achieving an intimate admixture. Pharmaceutical formulations comprising a stabilized azithromycin composition and methods of making such formulations are also described.

59 Claims, 2 Drawing Sheets

STABILIZED AZITHROMYCIN COMPOSITIONS

CROSS-REFERENCE TO RELATED APPLICATIONS

This application claims priority under 35 U.S.C. §119(e) to U.S. provisional application serial No. 60/336,346, filed Oct. 18, 2001; No. 60/331,931, filed Nov. 21, 2001; and, No. 60/341,295, filed Dec. 17, 2001. The entire content of each of these applications is incorporated herein by reference.

FIELD OF THE INVENTION

This invention relates to stabilized azithromycin compositions, methods of preparing stabilized azithromycin compositions, pharmaceutical formulations containing the stabilized azithromycin compositions and methods of making such formulations.

BACKGROUND OF THE INVENTION

The first of the macrolide antibiotics, erythromycin, was discovered in 1952 among the metabolic products of *Streptomyces erythreus*. Erythromycin is most effective against Gram-positive bacteria. Erythromycin has low acid stability which reduces its oral bioavailability and necessitates enteric coating of the drug.

Azithromycin, (2R,3S,4R,5R,8R,10R,11R,12S,13S,14R)-13-[(2,6-dideoxy-3-C-methyl-3-O-methyl-α-L-ribo-hexopyranosyl)oxy]-2-ethyl-3,4,10-trihydroxy-3,5,6,8,10,12,14-heptamethyl-11-[[3,4,6-trideoxy-3-(dimethyl amino)-β-D-xylo-hexopyranosyl]oxy]-1-Oxa-6-azacyclopentadecan-15-one, may be considered a second generation macrolide antibiotic.

Azithromycin is subject to degradation that can occur during manufacture and storage. In particular, the amine group of azithromycin is susceptible to oxidation. For example, azithromycin is susceptible to degradation if exposed to elevated temperatures and/or air during manufacturing processes, including processes of formulating pharmaceutical dosage forms of azithromycin. This could cause the drug product to deviate from regulatory purity requirements even before the product reaches doctors and patients. Additionally, once formulated, azithromycin has a tendency to degrade under normal storage conditions, which may result in an unacceptable level of impurities at the time of administration.

Thus, there exists a need for improved azithromycin compositions and methods of manufacturing such compositions in which the tendency for degradation of the azithromycin is reduced, resulting in azithromycin compositions with a higher degree of purity.

SUMMARY OF THE INVENTION

Figure 1:
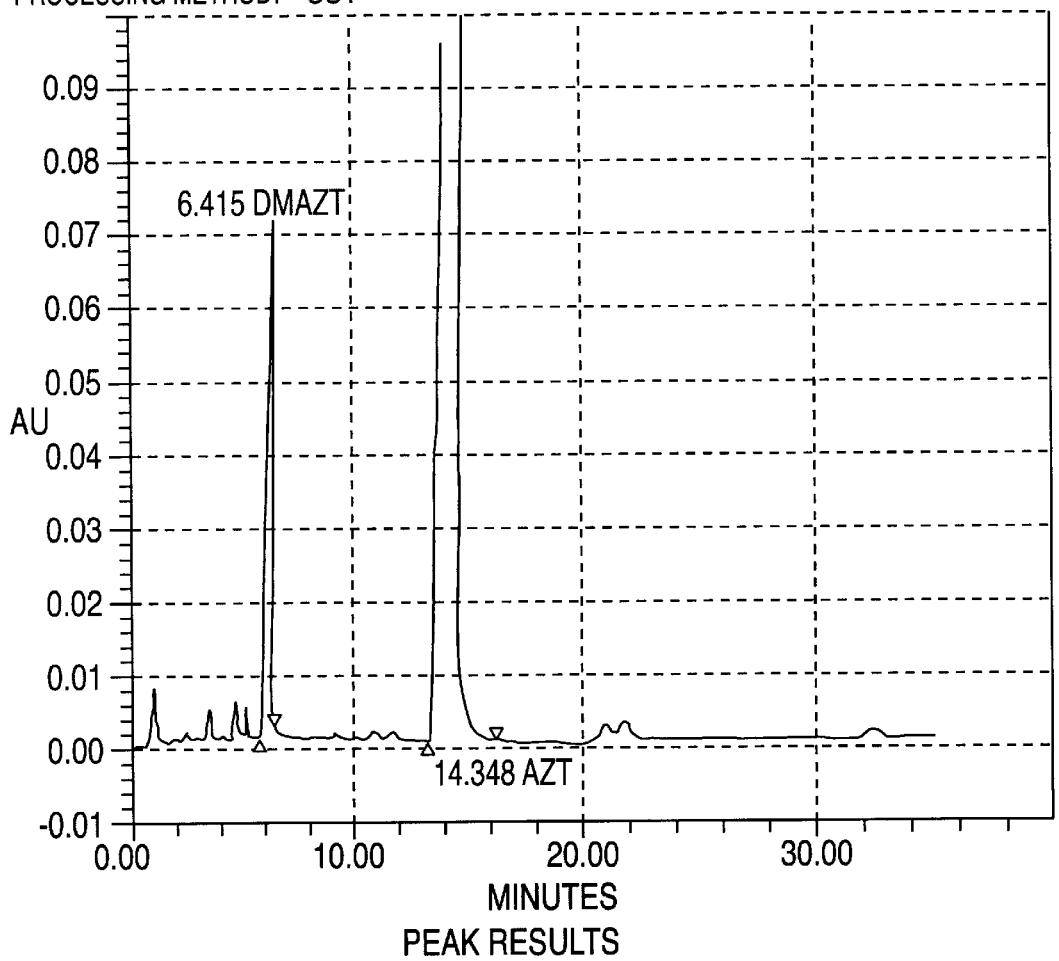
FIG. 1 is an HPLC chromatogram depicting elution profiles of azithromycin standards.
Figure 2:
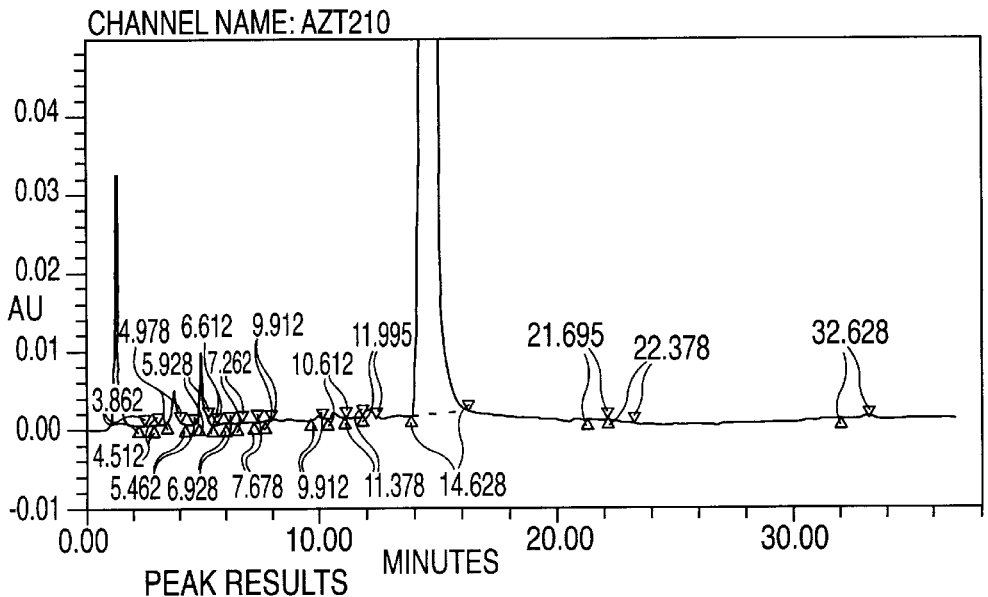
FIG. 2 is an HPLC chromatogram depicting typical elution profiles of azithromycin impurities.

One embodiment of the invention is directed to stabilized azithromycin compositions. A stabilized azithromycin composition preferably includes an intimate admixture of azithromycin and a stabilizing-effective amount of an antioxidant. Coprecipitation and co-milling of azithromycin and an antioxidant are particularly preferred methods of achieving an intimate admixture.

Another embodiment of the invention is directed to a method for preparing a stabilized azithromycin composition. The method comprises dissolving azithromycin and a stabilizing-effective amount of an antioxidant in a solvent and co-precipitating the azithromycin and antioxidant, and, recovering a stabilized azithromycin composition.

Stabilized azithromycin compositions can also be prepared by dissolving azithromycin and a stabilizing-effective amount of an antioxidant in a first solvent to form a mixture; drying the mixture; redissolving the mixture in a second solvent; co-precipitating azithromycin and the antioxidant and recovering a stabilized azithromycin composition.

Yet another method for making a stabilized azithromycin composition in accordance with the present invention includes co-milling azithromycin and a stabilizing-effective amount of an antioxidant. In this embodiment, co-milling may be achieved by, for example, grinding the azithromycin and antioxidant together by conventional means such as using a mortar and pestle or co-micronization processes as are generally known in the art.

Once a stabilized azithromycin composition is prepared in accordance with the present invention, it is preferably formulated into pharmaceutical formulations such as conventional dosage forms, including tablets, capsules (e.g., hard and soft gelatin capsules), suspensions, sachets, dragees, suppositories, etc. Tablets are preferred dosage forms. Tablets may be made with the stabilized azithromycin compositions and optional excipients by processes including, e.g., wet granulation, dry granulation such as slugging or compaction, or direct compression, followed by shaping into tablets.

DESCRIPTION OF THE PREFERRED EMBODIMENTS

Definitions

As used herein, the term "AZT" refers to azithromycin. The term "DMAZT" refers to azaerythromycin A (USP), desmethyl azithromycin. DMAZT is an intermediate used in the synthesis of azithromycin. The term "TAZT" refers to tosyl azithromycin. The term "BH" refers to butylated hydroxyanisole. The term "BHT" refers to butylated hydroxytoluene. The term "PG" refers to propyl gallate. The term "PVP" refers to polyvinylpyrrolidone. The term "SLS" refers to sodium lauryl sulfate. The term "API" refers to active pharmaceutical ingredient. The term "LOD" refers to loss on dry.

Unless otherwise indicated, the term "azithromycin" includes the salts, hydrates, solvates and physiologically functional derivatives thereof. The term also includes all polymorphous forms.

The term "stabilizing-effective amount," used in reference to the amount of antioxidant in the stabilized azithromycin composition, means (1) an amount such that no more than about 3.8%, preferably no more than about 1.2%, and, most preferably, no more than about 0.86% by weight of azithromycin in the stabilized azithromycin composition is degraded upon exposure to 55° C. for seven days or, (2) an amount such that no more than about 1.25%, preferably no more than about 0.8%, and, most preferably, no more than about 0.35% by weight of azithromycin in the stabilized azithromycin composition is degraded upon exposure to 50° C. for 20 hours.

Azithromycin degrades when exposed to temperatures above about 25° C. It has now been found that the addition of antioxidants to azithromycin protects azithromycin from degradation at elevated temperatures, which may be due to oxidation and/or other means.

In one aspect, the present invention is directed to a stablized azithromycin composition. In several embodiments, the azithromycin used is azithromycin ethanolate monohydrate. Azithromycin ethanolate monohydrate is a stable azithromycin compound disclosed in U.S. Pat. No. 6,365,574, which is incorporated herein by reference.

In one embodiment, the stabilized azithromycin composition comprises azithromycin and an stabilizing-effective amount of an antioxidant. As used herein, "antioxidant" refers to a substance known to inhibit oxidation. Among preferred antioxidants suitable for use in accordance with the present invention are included ascorbic acid, sodium ascorbate, calcium ascorbate, ascorbic palmitate, butylated hydroxyanisole, butylated hydroxytoluene, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is a food grade antioxidant, however any antioxidant which is generally recognized as pharmaceutically acceptable may be used.

More preferably, the antioxidant is butylated hydroxyanisole, butylated hydroxytoluene, propyl gallate, ascorbic acid, pharmaceutically acceptable salts or esters thereof, or mixtures thereof. Most preferably, the antioxidant is butylated hydroxytoluene or sodium ascorbate.

Preferably, the antioxidant is present in the stabilized azithromycin compositions in an effective amount to retard or prevent degradation of azithromycin, thereby stabilizing the azithromycin. Preferably, the amount of antioxidant is in the range of about 0.01–10% by weight azithromycin. More preferably, the amount of antioxidant is in the range of about 0.1–5% by weight azithromycin. In preferred embodiments, (1) the amount of antioxidant used is such that no more than about 3.8%, preferably no more than about 1.2%, and, most preferably, no more than about 0.86% by weight of azithromycin in the stabilized azithromycin composition is degraded upon exposure to 55° C. for seven days, or (2) the amount of antioxidant used is such that no more than about 1.25%, preferably no more than about 0.8%, and, most preferably, no more than about 0.35% by weight of azithromycin in the stabilized azithromycin composition is degraded upon exposure to 50° C. for 20 hours.

In another aspect, the present invention is directed to a method for manufacturing a stabilized azithromycin composition.

In one embodiment, the stabilized azithromycin composition is made by the addition of an antioxidant to a solution of azithromycin before crystallizing the azithromycin from the solution. Upon crystallization, a co-precipitate of azithromycin and antioxidant is formed and recovered from the solution. The co-precipitate comprises azithromycin and antioxidant in intimate admixture. The stabilized composition of azithromycin may then be formulated into suitable dosage forms with conventional excipients.

In another embodiment, the stabilized azithromycin composition is made by the addition of an antioxidant to an azithromycin solution at the onset of crystallization of azithromycin from the solution. A co-precipitate of azithromycin and antioxidant is formed and recovered from the solution. The co-precipitate comprises azithromycin and antioxidant in intimate admixture. The stabilized composition of azithromycin may then be formulated into suitable dosage forms with conventional excipients.

In yet another embodiment, a stabilized azithromycin composition is made by addition of an antioxidant to an azithromycin solution and the partial or total evaporation of the solvent. Preferably, this embodiment comprises the steps of: 1) dissolving azithromycin and an antioxidant in a first solvent; 2) evaporating the first solvent to form a dry residue; 3) redissolving the dry residue in a second (not necessarily different) solvent; 4) crystallizing azithromycin and 5) adding additional antioxidant at the onset of crystallization. A co-precipitate of azithromycin and antioxidant is formed and recovered from the solution. The co-precipitate comprise azithromycin and antioxidant in intimate admixture. The stabilized composition of azithromycin may then be formulated into suitable dosage forms with conventional excipients.

The preferred solvent in the disclosed methods is an alcohol. More preferably, the solvent is a lower straight or branched-chain alkanol such as ethanol, propanol, isopropanol, etc.

In still another embodiment, a stabilized azithromcyin composition is made by co-milling azithromycin and antioxidant to form an intimate admixture. Co-milling may be done by grinding the azithromycin and antioxidant using conventional methods such as with a mortar and pestle or by co-micronizing the azithromycin and antioxidant.

In another aspect, the present invention is directed to pharmaceutical formulations comprising a stabilized azithromycin composition as described herein and methods for making such pharmaceutical formulations. The pharmaceutical formulations typically contain, in addition to the stabilized azithromycin composition, one or more pharmaceutically acceptable excipients, such as binders, fillers, disintegrants, carriers, lubricants, glidants, flavorants, colorants, buffers, thickening agents, etc. Some excipients can serve multiple functions, for example as both binder and disintegrant.

The pharmaceutical formulations comprising a stabilized azithromycin composition include dosage forms such as tablets, granulates, dragees, hard or soft capsules, powders, solutions, emulsions, suspensions, or the like. Tablets are particularly preferred dosage forms of the pharmaceutical formulations in accordance with the present invention. Among the methods for forming preferred tablet dosage forms are included, e.g., wet granulation, dry granulation, e.g., compaction and slugging, and direct compression.

Examples of tablet disintegrants useful in accordance with the present invention are starch, pregelatinized starch, sodium starch glycolate, sodium carboxymethylcellulose, crosslinked sodium carboxymethylcellulose (sodium croscarmellose; crosslinked starch available under the registered trademark Ac-Di-Sol from FMC Corp., Philadelphia, Pa.), clays (e.g. magnesium aluminum silicate), microcrystalline cellulose (of the type available under the registered trademark Avicel from FMC Corp. or the registered trademark Emcocel from Mendell Corp., Carmel, N.Y.), alginates, gums, surfactants, effervescent mixtures, hydrous aluminum silicate, cross-linked polyvinylpyrrolidone (available commercially under the registered trademark PVP-XL from International Specialty Products, Inc.), and others as known in the art.

Among preferred disintegrants are sodium croscarmellose (Ac-Di-Sol), sodium starch glycolate (available commercially under the registered trademarks Primojel from Avebe (Union, N.J.) or Generichem, (Little Falls, N.J.), pregelatinized starch and Explotab from Mendell Corp.), microcrystalline cellulose (Avicel), and cross-linked polyvinylpyrrolidone (PVP-XL).

Examples of binders include, e.g., acacia, cellulose derivatives (such as methylcellulose and carboxymethylcellulose, hydroxypropylmethylcellulose, hydroxypropylcellulose, hydroxyethylcellulose), gelatin, glucose, dextrose, xylitol, polymethacrylates, polyvinylpyrrolidone, starch paste, sucrose, sorbitol, pregelatinized starch, gum tragacanth, alginic acids and salts thereof such as sodium alginate, magnesium aluminum silicate, polyethylene glycol, guar gum, bentonites, and the like.

Flavors incorporated in the composition may be chosen from synthetic flavor oils and flavoring aromatics and/or natural oils, extracts from plants leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Generally the flavoring will be present in an amount of from 0.5 to about 3.0 percent by weight based on the total tablet weight, when a flavor is used.

A variety of materials may be used as fillers or diluents. Examples are spray-dried or anhydrous lactose, sucrose, dextrose, mannitol, sorbitol, starch (e.g. starch 1500), cellulose (e.g. microcrystalline cellulose; Avicel), dihydrated or anhydrous dibasic calcium phosphate (available commercially under the registered trademark Emcompress from Mendell or A-Tab and Di-Tab from Rhone-Poulenc, Inc., Monmouth Junction, N.J.), calcium carbonate, calcium sulfate, and others as known in the art. A preferred filler in accordance with the present invention is dibasic calcium phosphate dihydrate or anhydrous.

Lubricants can also be employed herein in the manufacture of certain dosage forms, and will usually be employed when producing tablets. Examples of lubricants are magnesium stearate, talc, stearic acid, glycerylbehenate, polyethylene glycol, ethylene oxide polymers (for example, available under the registered trademark Carbowax from Union Carbide, Inc., Danbury, Conn.), sodium lauryl sulfate, magnesium lauryl sulfate, sodium oleate, sodium stearyl fumarate, DL-leucine, colloidal silica, and others as known in the art. Preferred lubricants are magnesium stearate, and mixtures of magnesium stearate with sodium lauryl sulfate. Lubricants generally comprise 0.5 to 7.0% of the total tablet weight.

Other excipients such as glidants and coloring agents may also be added to azithromycin tablets. Coloring agents may include titanium dioxide and/or dyes suitable for food such as those known as F. D. & C, dyes and natural coloring agents such as grape skin extract, beet red powder, beta carotene, annato, carmine, turmeric, paprika, and so forth. A coloring agent is an optional ingredient in the compositions of this invention, but when used will generally be present in an amount up to about 3.5 percent based on the total tablet weight.

As known in the art, tablet blends may be dry-granulated or wet granulated before tableting. Alternatively, tablet blends may be directly compressed. The choice of processing approach depends upon the properties of the drug and chosen excipients, for example particle size, blending compatibility, density and flowability. For azithromycin tablets, granulation is preferred, with wet granulation being most preferred. The stabilized azithromycin composition may be wet-granulated, and then other excipients may be added extragranularly. Alternatively, the stabilized azithromycin composition and one or more excipients may be wet-granulated. Dry granulation, such as compaction and/or slugging with or without an intragranular excipient may also be used to make the tablets, followed by tabletting with or without extragranular excipients. In addition, tablets may also be coated, with a coating that exhibits little or no effect on or interference with tablet dissolution, to assure ease of swallowing or to provide an elegant appearance.

Tablets may be film-coated to provide ease of swallowing and an elegant appearance. Many polymeric film-coating materials are known in the art, including, e.g., hydroxypropylmethylcellulose (HPMC). HPMC may be obtained commercially, for example from Colorcon Corp., in coating formulations containing excipients which serve as coating aids, under the registered trademark Opadry. Opadry formulations may contain lactose, polydextrose, triacetin, polyethyleneglycol, polysorbate 80, titanium dioxide, and one or more dyes or lakes. Other suitable film-forming polymers also may be used herein, including, hydroxypropylcellulose, and acrylate-methacrylate copolymers.

Conventional tableting processes are employed, e.g., by forming a tablet from a desired blend or mixture of ingredients into the appropriate shape using a conventional tablet press. Tablet formulation and conventional processing techniques have been widely described, for Example in Pharmaceutical Dosage Forms: Tablets; Edited By Lieberman, Lachman, and Schwartz; Published by Marcel Dekker, Inc., 2d Edition, Copyright 1989, the text of which is herein incorporated by reference.

The azithromycin dosage forms of this invention also include powders to make oral suspensions, and also the oral suspensions themselves. Generally the powder is a non-caking, free flowing powder which is sold direct to pharmacies or other retail outlets and then made up into the actual suspension by a pharmacist. The oral suspension is thus the actual dosage form ingested by patients.

Azithromycin suspensions may contain, e.g., in addition to a stabilized azithromycin composition, one or more thickening agents, a buffer or pH-altering agent. Dispersing agents may also be used to facilitate formation of a suspension.

Suitable thickening agents function as suspending agents and include, for example, hydrocolloid gums known for such purpose, examples of which include xanthan gum, guar gum, locust bean gum, gum tragacanth, and the like. Alternatively, synthetic suspending agents may be used such as sodium carboxymethylcellulose, polyvinylpyrrolidone, hydroxypropylcellulose and the like. Dispersing agents include colloidal silicon dioxide, available from Cabot Corporation, Boston, Mass. under the trade designation Cab-O-Sil.

A powder used to make a suspension may also contain conventional optional ingredients such as (1) wetting agents such as sorbitan monolaurate, polysorbate 80, and sodium lauryl sulfate; (2) anti-foaming agents and (3) sweeteners and fillers such as glucose. The powder may also contain a buffer to maintain a high pH upon reconstitution, as discussed above. Suitable buffers and pH-altering agents include tribasic sodium phosphate, anhydrous sodium carbonate, glycine, and the like. Suitable preservatives are well known, for example sodium benzoate and the like.

A stabilized azithromycin composition in accordance with the present invention may be formulated in a unit dose packet dosage form or sachet. Such a packet will typically contains a blend of azithromycin and excipients which is thus reconstituted. In addition to a stabilized azithromycin composition in accordance with the present invention, the packet may contain, for example, a dispersing agent which makes the sachet powder free flowing, for example colloidal silicon dioxide such as Cab-O-Sil from Cabot. The dispersing agent may also serve as a glidant. The formulation may also optionally contain ingredients including (1) a filler or sweetener (e.g. glucose); (2) a buffer (e.g. sodium phosphate); (3) a wetting agent such as a surfactant, for example sodium lauryl sulfate, and (4) flavors such as any of those enumerated herein, and the like. The powder in the packet flows freely and disperses quickly, essentially immediately upon stirring when reconstituted.

Although the following examples illustrate the practice of the present invention in some of its embodiments, the examples should not be construed as limiting the scope of the invention. Other embodiments will be apparent to one skilled in the art from consideration of the specification and examples.

EXAMPLES

General

The dibasic calcium phosphate dihydrate used was Emcompress®, which is available from Penwest Pharmaceuticals Co., Cedar Rapids, Iowa. The sodium starch glycolate used was Explotab®, which is also available from Penwest Pharmaceuticals. Sodium lauryl sulfate was used as received from Cognis (Henkel). The povidone used was povidone K-25 as received from ISP Pharmaceuticals. The colloidal silicon dioxide used was either Cab-O-Sil®, available from Astro Chemicals Inc., Springfield, Mass., or Aerosil 200®, available from Degussa. The dibasic calcium phosphate used was A-Tab®, which is available from Rhodia (Rhone Poulenc). The pregelatinized starch used was Starch 1500®, which is available from Colorcon. The croscarmellose sodium used was Ac-Di-Sol®, which is available from Farma International. The tablet coating used was Opadry®, which is available from Colorcon. The xanthan gum used is available from Kelco.

Quantitation Method Used in Accelerated Stability Studies

The quantity of impurities present before and after oxidative stress were quantified by high performance liquid chromatography, employing the following conditions:

| | |
|---|---|
| Column: | RP18, 5µ, 150 × 4.6 mm |
| Eluent: | 40% 0.05 M of potassium hydrogen phosphate (K$_2$HPO$_4$) adjusted to pH 8.2 with 20% phosphoric acid; 60% acetonitrile |
| Flow rate: | 0.9 ml min$^{-1}$ |
| Detection: | UV, λ = 210 nm |
| Column Temp.: | 30° C. |
| Sample | |
| Volume: | 50 µl |
| Diluent: | Same as Eluent |

Sample solutions were freshly prepared from azithromycin and injected on column.

The percentages of impurities were calculated from the integrator output.

Performance Evaluation

The performance of the HPLC system was tested using standardized solutions of AZT and DMAZT.

Example 1

Admixtures of Azithromycin and BHT

Mixtures of azithromycin and BHT were prepared using various methods of admixing to assess their effectiveness at inhibiting degradation of azithromycin.

Preparative

Preparation 1 [CS Ex. 1: Precipitated]

Technical grade azithromycin (10 g, 13 mmol) and BHT (0.18 g, 0.82 mmol, 6.1 mole %) were dissolved in absolute ethanol (30 ml) at 20° C. in a 250 ml three-necked flat flanged jacketed vessel equipped with a mechanical stirrer, a condenser and thermometer. Water (3 ml) was added at 20° C. and the solution was heated at a constant 9° C. h$^{-1}$ temperature gradient to 55° C. over about 4 hours. More water (11 ml) was slowly added to the vessel at between 35° C. and 55° C., which caused a precipitate to form. The resulting suspension was maintained at 55° C. for another two hours. During this time interval more water (49 ml) was added to the suspension. The suspension was then cooled at a constant temperature gradient from 55° C. to 20° C. over 2 hours and filtered at 20° C. After drying, a stable dry product (9 g, 90%) was obtained.

Preparation 2 [CS Ex. 2: Added at Cloudiness]

Technical grade azithromycin (10 g, 13.35 mmol) was dissolved in absolute ethanol (30 ml) at 20° C. in a 250 ml three-necked flat flanged jacketed vessel equipped with a mechanical stirrer, a condenser and thermometer. Water (3 ml) was added at 20° C. and the solution was heated at a constant 9° C. h$^{-1}$ temperature gradient to 55° C. over about 4 hours. More water (11 ml) was slowly added to the vessel at between 35° C. and 55° C. Azithromycin began to precipitate from the solution at 46° C. BHT (0.18 g, 0.82 mmol, 6.1 mole %) was added at the first sign of cloudiness. After reaching 55° C., the suspension was maintained at that temperature for another two hours, over which time more water (49 ml) was added. The suspension was then cooled at a constant 18° C. h$^{-1}$ temperature gradient from 55° C. to 20° C. over about 2 hours and then filtered at 20° C. A stable dry product (9 g, 90%) was obtained after drying.

Preparation 3 [CS Ex. 3: Portion Evaporated Portion Added at Cloudiness]

Technical grade azithromycin (10 g, 13 mmol) and BHT (0.12 g, 0.54 mmol, 4.1 mole %) were dissolved in absolute ethanol (30 ml) at 20° C. in a 250 ml three-necked flat flanged jacketed vessel equipped with a mechanical stirrer, a condenser and thermometer. The ethanol was evaporated and the dry residue was taken up in fresh absolute ethanol (20 ml). Water (3 ml) was added at 20° C. and the solution was heated at a constant 9° C. h$^{-1}$ temperature gradient to 55° C. over about 4 hours. More water (11 ml) was slowly added to the vessel at between 35° C. and 55° C. Azithromycin began to precipitate from the solution at 46° C. BHT (180 mg, 0.82 mmol, 6.1 mole %) was added at the first sign of cloudiness. After reaching 55° C., the suspension was maintained at that temperature for another two hours, over which time more water (49 ml) was added. The suspension was cooled at a constant temperature gradient of 18° C. h$^{-1}$ from 55° C. to 20° C. over about 2 hours and then filtered at 20° C. A stable dry product (9 g, 90%) was obtained after drying.

Preparation 4 [Milling]

Azithromycin (1 g, 1.3 mmol) was weighed out and set aside. BHT (12 mg, 0.054 mmol, 4.1 mole %) was finely milled with a mortar and pestle. The azithromycin was added portionwise to the BHT. Each portion was thoroughly milled with the BHT using the mortar and pestle.

Preparation 5 [Comparative]

In this example, no antioxidant was used. In other respects, the azithromycin was processed according to Preparation 1 and the resulting product was used as a control sample against which to compare the degradation rates of stabilized azithromycin compositions.

Methodology

Samples of azithromycin admixtures prepared according to preparations 1–5 were analyzed by HPLC for impurity content immediately after their preparation by mixing with an appropriate quantity of eluent to give an approximately 4 mg/ml clear solution. Another sample of each of the preparations was stored at 55° C. The vial contents were analyzed by HPLC seven days after being placed in the oven.

Results

The results of the accelerated stability study on stabilized azithromycin are recorded in Table 1.

Preparative

Preparation 6 [RM 2206]

Technical grade azithromycin was recrystallized from ethanol. No anti-oxidants were added.

Preparation 7 [T 582-02]

Technical grade azithromycin (300 g, 400 mmol) was recrystallized from ethanol. BHT (1.2 g, 5.4 mmol, 1.4 mole %) was dissolved in ethanol and the solution was sprayed onto the azithromycin with thorough mixing.

Preparation 8 [T 592-03]

Technical grade azithromycin (300 g, 400 mmol) was recrystallized from ethanol. BHT (1.2 g, 5.4 mmol, 1.4 mole

TABLE 1

Comparison of Degradation of Azithromycin stabilized with BHT and without Stabilization Upon Exposure to 55° C.

| Preparation | BHT (mole %) | Total Impurities Before Exposure (% Area) | Exposure Time (Days) | Total Impurities After Exposure (% Area) | Percent Change | Method of Admixing |
| --- | --- | --- | --- | --- | --- | --- |
| 1 | 6.1 | 0.66 | 7 | 1.16 | 0.50 | AZT and BHT co-precipitated from solution |
| 2 | 6.1 | 0.88 | 7 | 0.98 | 0.10 | Precipitation of AZT from a suspension of BHT |
| 3 | 4.1 | 0.66 | 7 | 0.86 | 0.20 | Co-precipitation of AZT and BHT from a suspension of BHT |
| 4 | 4.1 | 0.25 | 16 | 1.03 | 0.78 | Milling |
| 5 | — | 0.27 | 7 | 3.76 | 3.49 | No BHT was used |

The four different techniques of intimately admixing azithromycin and BHT used in Preparations 1–4 led to a significant reduction in impurity content, relative to the control, after the admixture was subjected to oxidative stress. The stability results suggest that degradation occurs by an oxidation pathway because of the general inhibition achieved by adding the free radical inhibitor BHT. The degrees of inhibition observed using the different techniques of admixing are significantly different. Comparison of the results from Preparations 1 and 2 shows that oxidation is inhibited somewhat more effectively by adding the stabilizer as soon as the azithromycin begins to precipitate from the ethanolic solution, rather than before, but that both techniques are highly effective. It is believed that addition of the stabilizer at the time that the azithromycin begins to precipitate from the solution may be more effective relative to addition of the stabilizer before precipitation because the stabilizer or antioxidant (such as BHT) is more effectively entrapped within the already formed crystals and consequently has increased protective activity. If the crystals are not yet formed, the stabilizer or antioxidant is more easily washed out by the solvent. Comparison of the results from Preparations 2 and 3 shows that the anti-oxidant inhibiting effect of BHT did not diminish over time. The best results of azithromycin stabilization were achieved by forming a stabilized azithromycin composition by co-milling of azithromycin and an antioxidant such as BHT.

Example 2
Admixtures of Azithromycin and Food Grade Antioxidants

The inhibiting effect of food grade antioxidants was explored at yet lower concentrations and with other mixing methods.

%) and PG (1.2 g, 5.7 mmol, 1.4 mole %) were dissolved in ethanol and the solution was sprayed onto the azithromycin with thorough mixing.

Preparation 9 [T 582-04]

Technical grade azithromycin (300 g, 400 mmol) was dissolved in ethanol and a solution of BHT (1.2 g, 5.4 mmol, 1.4 mole %) in ethanol was combined with the azithromycin solution. The ethanol was then evaporated leaving a residue of azithromycin and BHT in intimate admixture.

Preparation 10 [T 582-05]

Technical grade azithromycin (300 g, 400 mmol) was dissolved in ethanol and a solution of BHT (1.2 g, 5.4 mmol, 1.4 mole %) and PG (1.2 g, 5.7 mmol, 1.4 mole %) was combined with the azithromycin solution. The ethanol was then evaporated leaving a residue of azithromycin, BHT and PG in intimate admixture.

Methodology

Preparations 6–10 were incubated at 25° C. and 50° C. for 20 hours under open cap conditions.

Results

The results of the accelerated stability study comparing azithromycin stabilized by co-precipitation with an antioxidant and granulation with an antioxidant-containing solution are reported in Table 2.

TABLE 2

Comparison of Degradation of Unstabilized Azithromycin, Azithromycin Stabilized by Wet Granulation with Antioxidant and Azithromycin Stabilized by Co-precipitation with an Antioxidant After Twenty Hours at Ambient or Elevated Temperature

| Preparation | Temp (° C.) | Antioxidant (mole %) | % Impurity 1 (RRT[a] ≈ 0.23) | % Impurity 2 (RRT[a] ≈ 0.30) | % Impurity 3 (RRT[a] ≈ 0.34) | % Impurity 4 (RRT[a] ≈ 0.76) | Total Impurity | Method of Mixing |
| --- | --- | --- | --- | --- | --- | --- | --- | --- |
| 6[b] (unstabilized) | 25 | — | 0.07 | 0.19 | 0.09 | 0.03 | 0.38 | Antioxidant was not added. |
| | 50 | | 0.30 | 0.50 | 0.16 | 0.16 | 1.12 | |

TABLE 2-continued

Comparison of Degradation of Unstabilized Azithromycin, Azithromycin Stabilized by Wet Granulation with Antioxidant and Azithromycin Stabilized by Co-precipitation with an Antioxidant After Twenty Hours at Ambient or Elevated Temperature

| Preparation | Temp (° C.) | Anti-oxidant (mole %) | % Impurity 1 (RRT$^a$ ≈ 0.23) | % Impurity 2 (RRT$^a$ ≈ 0.30) | % Impurity 3 (RRT$^a$ ≈ 0.34) | % Impurity 4 (RRT$^a$ ≈ 0.76) | Total Impurity | Method of Mixing |
|---|---|---|---|---|---|---|---|---|
| 7 | 25 | BHT (1.4$^b$) | 0.07 | 0.24 | 0.08 | 0.05 | 0.44 | Azithromycin granulated with |
|   | 50 |  | 0.32 | 0.52 | 0.22 | 0.16 | 1.22 | an ethanolic solution of antioxidant. |
| 8 | 25 | BHT (1.4) | 0.06 | 0.21 | 0.06 | 0.04 | 0.37 | Azithromycin granulated with |
|   | 50 | & PG (1.4) | 0.28 | 0.38 | 0.27 | 0.15 | 1.08 | an ethanolic solution of antioxidant. |
| 9 | 25 | BHT (1.4) | 0.09 | 0.22 | 0.07 | 0.03 | 0.41 | Co-precipitation of AZT and |
|   | 50 |  | 0.08 | 0.22 | 0.08 | 0.06 | 0.44 | antioxidant |
| 10 | 25 | BHT (1.4) | 0.08 | 0.20 | 0.08 | 0.03 | 0.39 | Co-precipitation of AZT and |
|   | 50 | & PG (1.4) | 0.08 | 0.22 | 0.08 | 0.06 | 0.44 | antioxidants |

$^a$RRT = relative retention time
$^b$1.4 mole % corresponds to approximately 0.4 weight percent for both BHT and PG As can be seen by comparison of the results obtained from Preparations 9 and 10 with those obtained from Preparations 6 and 7, the use of antioxidants resulted in less degradation when the antioxidants were co-precipitated with azithromycin versus granulating azithromycin with an ethanolic solution containing the antioxidants. Degradation of the untreated azithromycin was most significant at elevated temperature, yet elevated temperature had little effect upon the degradation rate of azithromycin that was coprecipitated with an antioxidant (Preparations 9 and 10). In addition, the mode of application of the antioxidant is more important to achieving the inhibiting effect than the amount of antioxidant used (compare the total impurity content of Preparations 8, 9 and 10 after twenty hours at 50° C.).

Example 3

Wet Granulated Tablet of Stabilized Azithromycin

In addition to studying the stability of mixtures highly concentrated in azithromycin (i.e., mixtures of azithromycin and an antioxidant), we studied the stability of azithromycin in representative pharmaceutical compositions and dosage forms containing antioxidant mixed with AZT in various ways.

Formulations

Formulation 1 [T 582-02]

Stabilized azithromycin resulting from Preparation 7 was formulated into a wet granulated tablet following the stepwise procedure below using the components in Table 3.

TABLE 3

| No | Components | mg/Tablet | Wt. % | Per Batch (g) |
|---|---|---|---|---|
| 1 | Preparation 7 (AZT granulated with BHT soln.) | 270 | 58.35% | 219.12 |
| 2 | Dibasic Calcium phosphate dihydrate | 30 | 6.48 | 24.28 |
| 3 | Sodium starch glycolate | 9.4 | 2.03 | 7.61 |
| 4 | Sodium lauryl sulfate (SLS) | 3.13 | 0.68 | 2.54 |
| 5 | Povidone K-25 (PVP) | 19 | 4.11 | 15.36 |
| 6 | Dibasic Calcium Phosphate Dihydrate | 115 | 24.90 | 92.95 |
| 7 | Sodium starch glycolate (SSG) | 9.4 | 2.03 | 7.61 |
| 8 | Magnesium stearate | 4.75 | 1.03 | 3.82 |
| 9 | Colloidal silicon dioxide (Cab-O-Sil ®) | 2.09 | 0.45 | 1.69 |
|   | Total | 462.7 | 100.00 | 347.98 |
| 10 | BHT in Azithromycin: | 1.08 | 0.23 | 0.88 |
| 11 | Alcohol 2A (removed in processing) |  |  | 40 |

1. A solution of SLS (2.54 g) and PVP K-25 (15.36 g) was prepared in denatured alcohol formula 2A (40 g) (see USP).
2. Preparation 7 (220.0 g) was mixed in a polyethylene bag with dibasic calcium phosphate dihydrate and sodium starch glycolate.
3. The product of step 2 was transferred into a Hobart planetary mixer and granulated with the PVP-SLS solution of step 1 at low speed for 1 minute.
4. The granulate was passed through a hand screen (#8 mesh) and dried at 45° C. for 6 hours in a forced air oven.
5. The dried granulate of step 4 was passed through a hand screen (#16 mesh). The loss on drying (LOD) of the granulate was 2.9% (90° C.).
6. The screened granulate was additionally dried at 50° C. for 50 minutes at which point LOD = 1.6–1.9%.
7. The dried granulation of step 6 was mixed with the dibasic calcium phosphate dihydrate and SSG in a polyethylene bag for 2 minutes.
8. In a separate bag colloidal silicon dioxide was mixed with about 100 g of the granulate of step 7 and then passed through a hand screen (#16 mesh) and then combined with the remaining quantity of the granulate of step 7 and mixed for 1 minute in a polyethylene bag.
9. The magnesium stearate was combined with about 100 g of the granulate of step 8, passed through a hand screen (#16 mesh) and then combined with remaining quantity of step 8 and mixed for 1 minute in polyethylene bag.

Capsule-shape tablets were prepared from the granulate obtained after step 9 using 0.248×0.560 inch punches on a B3B Manesty tablet press.

Formulation 2 [T 582-03]

Formulation 2 was prepared using the same inactive ingredients and processing as per Formulation 1 but substituting Preparation 8 containing AZT granulated with an ethanolic solution containing 1.4 mole % of BHT and PG for Preparation 7. The formulation thus contained 0.23 wt. % of each of BHT and PG.

Formulation 3 [T 582-04]

Formulation 3 was prepared using the same inactive ingredients and processing as per Formulation 1 but substituting Preparation 9, a co-precipitate of AZT and 1.4 mole % BHT from an ethanolic solution, for Preparation 7. The formulation thus contained 0.23 wt. % of BHT.

Formulation 4 [T 582-05]

Formulation 4 was prepared using the same inactive ingredients and processing as per Formulation 1 but substituting Preparation 10, a co-precipitate of AZT, 1.4 mole % BHT, and 1.4 mole % PG, from an ethanolic solution, for Preparation 7. The formulation thus contained 0.23 wt. % of BHT and PG Methodology All tablets were stressed under "open cap" conditions at 50° C. for 184 h.

Results

The results of the accelerated stability study on tablets formulated with stabilized azithromycin are reported in Table 4.

TABLE 4

Comparison of Stability of Wet-Granulated Tablets Containing 250 mg Stabilized Azithromycin Prepared by Different Methods of Admixing The Azithromycin and Antioxidant Upon Exposure to 50° C.

| | | Antioxidant | Total Impurities (%) | | | | | |
|---|---|---|---|---|---|---|---|---|
| | | (Wt. % of | Before | | | Percent Change | | |
| Formulation | Preparation | Tablet) | Exposure | 66 h | 184 h | 66 h | 184 h | Method of Admixing |
| 1 | 7 | BHT (0.23%) | 0.47 | 1.51 | 2.55 | 1.04 | 2.08 | AZT granulated with ethanolic solution containing antioxidant. |
| 2 | 8 | BHT (0.23%) PG (0.23%) | 0.37 | 1.20 | 2.10 | 0.83 | 1.73 | AZT granulated with ethanolic solution containing antioxidant. |
| 3 | 9 | BHT (0.23%) | 0.38 | 0.71 | 1.17 | 0.33 | 0.79 | Co-precipitation of AZT and antioxidant. |
| 4 | 10 | BHT (0.23%) PG (0.23%) | 0.34 | 0.40 | 0.58 | 0.20 | 0.24 | Co-precipitation of AZT and antioxidant. |

The results recorded in Table 4 show that an intimate admixture of AZT and antioxidant obtained by co-precipitation is more effective at inhibiting degradation in a wet granulated tablet formulation than the application of the antioxidant during wet granulation of the AZT with other excipients.

Example 4

Azithromycin Tablet Prepared by Dry Granulation

The stability of dry granulated tablet formulations of azithromycin that were pre-compressed by roller compaction was also assessed in formulations with and without an added food grade antioxidant.

Formulations

Azithromycin was formulated into dry granulated 500 mg tablets following the stepwise procedure below using the excipients in Table 5.

TABLE 5

| | | Formulations (mg/Tablet) | | | | |
|---|---|---|---|---|---|---|
| Stage | Ingredients | 5 | 6 | 7 | 8 | 9 |
| Part I | Azithromycin | 525.3* | 525.3* | 525.3* | 525.3* | 525.3* |
| | Colloidal SiO$_2$ (Aerosil 200 ®) | 8.0 | 8.0 | 8.0 | 8.0 | 8.0 |
| | Propyl Gallate | — | 0.8 | — | — | — |
| | BHT | — | 0.8 | — | 0.4 | 0.8 |
| | Sodium Ascorbate | — | — | 1.6 | — | — |
| Part II | Dibasic Calcium Phosphate | 90.7 | 89.1 | 89.1 | 90.3 | 89.9 |
| | Pregelatinized Starch | 55.0 | 55.0 | 55.0 | 55.0 | 55.0 |
| | Croscarmellose Sodium | 18.0 | 18.0 | 18.0 | 18.0 | 18.0 |
| | Talc | 32.0 | 32.0 | 32.0 | 32.0 | 32.0 |
| | Magnesium Stearate | 2.0 | 2.0 | 2.0 | 2.0 | 2.0 |
| Part III | Colloidal SiO$_2$ (Aerosil 200 ®) | 10.0 | 10.0 | 10.0 | 10.0 | 10.0 |
| | Sodium Lauryl Sulfate | 2.4 | 2.4 | 2.4 | 2.4 | 2.4 |
| | Croscarmellose Sodium | 28.0 | 28.0 | 28.0 | 28.0 | 28.0 |

TABLE 5-continued

| | | Formulations (mg/Tablet) | | | | |
|---|---|---|---|---|---|---|
| Stage | Ingredients | 5 | 6 | 7 | 8 | 9 |
| | Talc | 13.6 | 13.6 | 13.6 | 13.6 | 13.6 |
| | Magnesium Stearate | 15.0 | 15.0 | 15.0 | 15.0 | 15.0 |
| Coating | Opadry ® | 24.0 | 24.0 | 24.0 | 24.0 | 24.0 |
| | Theoretical End Weight | 824.0 | 824.0 | 824.0 | 824.0 | 824.0 |

*525.3 mg of Azithromycin solvate is equivalent to 500 mg Azithromycin (based on the specific API potency of the particular lot used)

Formulation 5 [K-28201]
1. Part I materials were blended in a polyethylene bag and passed through an oscillating granulator (Frewitt®) equipped with a 1 mm aperture screen and loaded into a twin shelled Y-cone dry blender.
2. Part II materials were added to the Y-cone blender and mixed.
3. The mix was passed through a roller compactor.
4. The compact was twice passed through the oscillating granulator. In the first pass, the granulator was equipped with a 2 mm aperture screen. In the second pass, the granulator was equipped with a 1 mm aperture screen. The milled granulate was loaded into a Y-cone blender.
5. The Part III materials were added to the Y-cone blender and mixed.
6. Oval tablets 9×17 mm were pressed from the mixture on a Kilian RLS rotary tablet press.
7. A portion of the compressed tablets were coated with Opadry® II White. This formulation did not contain stabilizers.

Formulation 6 [K-28202]
Formulation 6 was processed using the same inactive ingredients and processing as per Formulation 5 except that 0.8 mg/tablet BHT and 0.8 mg/tablet PG were added in Step 1 and the amount of dibasic calcium phosphate used was reduced to give a tablet of identical theoretical end weight. Formulation 6 contained 0.1 wt. % BHT and 0.1 wt. % Propyl Gallate.

Formulation 7 [K-28483]
1. Part I materials were blended in a Diosna® P-10 high shear mixer.
2. Part II materials were added to the mixer and mixed.
3. The mix was passed through a roller compactor.
4. The compact was twice passed through a Frewitt. In the first pass, the Frewitt was equipped with a 2 mm aperture screen. In the second pass, the Frewitt was equipped with a 1 mm aperture screen. The milled granulate was loaded into a Y-cone blender.
5. The Part III materials were added to the Y-cone blender and mixed.
6. Oval tablets 9×17 mm were pressed from the mixture on a Kilian RLS rotary tablet press.
7. A portion of the compressed tablets were coated with Opadry® II White. The formulation contained 0.2 wt. % of Sodium Ascorbate.

Formulation 8 [K-28484]
Formulation 8 was processed using the same inactive ingredients and processing as per Formulation 7 except that 0.4 mg/tablet BHT was added to the Part I materials in lieu of 1.6 mg/tablet sodium ascorbate and the amount of dibasic calcium phosphate was adjusted to yield a tablet of identical weight. Formulation 8 contained 0.05 wt. % of BHT.

Formulation 9 [K-28485]
Formulation 9 was processed using the same inactive ingredients and processing as per Formulation 8 except that 0.8 mg/tablet BHT was added in Step 1 and the amount of dibasic calcium phosphate was reduced by 0.4 mg/tablet. Formulation 9 contained 0.1 wt. % of BHT.

Methodology
Tablets were stressed under a variety of storage conditions: in blister packs, in high density polyethylene (HDPE) bottles, and in aluminum laminated bags. The containers were filled and then sealed under ordinary atmosphere. The tablets were stored for five or seven days at 55° C.

Results
The results of the accelerated stability study on tablets prepared by dry granulation with pre-compression by roller compaction are reported in Table 6.

TABLE 6

Stability of Dry-Granulated 500 mg Azithromycin Tablets Pre-Compressed by Roller Compaction to Storage at 55° C. in Conventional Pharmaceutical Packaging and with or Without Different Food Grade Antioxidants Formulated in the Tablets

| Formulation | Storage Conditions | Stabilizer (Wt. % of Tablet) | Exposure Time (Days) | Total Impurities By HPLC (% Area) | | |
|---|---|---|---|---|---|---|
| | | | | Before Exposure | After Exposure | Change |
| 5 (coated) | Blister Pack | — | 5 | 0.7 | 1.3 | 0.6 |
| 5 (coated) | HDPE Bottle | — | 5 | 0.7 | 1.9 | 1.2 |
| 6 (coated) | Blister Pack | BHT (0.1) & PG (0.1) | 5 | 0.4 | 0.6 | 0.2 |
| 6 (coated) | HDPE Bottle | BHT (0.1) & PG (0.1) | 5 | 0.4 | 0.6 | 0.2 |
| 7 (coated) | Aluminum Laminate Bag | SA (0.2) | 7 | 0.3 | 0.8 | 0.5 |
| 7 (uncoated) | Aluminum Laminate Bag | SA (0.2) | 7 | 0.6 | 0.9 | 0.3 |
| 8 (coated) | Aluminum Laminate Bag | BHT (0.05) | 7 | 0.2 | 0.6 | 0.4 |
| 8 (uncoated) | Aluminum Laminate Bag | BHT (0.05) | 7 | 0.4 | 0.7 | 0.3 |

TABLE 6-continued

Stability of Dry-Granulated 500 mg Azithromycin Tablets Pre-Compressed by Roller
Compaction to Storage at 55° C. in Conventional Pharmaceutical Packaging and
with or Without Different Food Grade Antioxidants Formulated in the Tablets

| Formulation | Storage Conditions | Stabilizer (Wt. % of Tablet) | Exposure Time (Days) | Total Impurities By HPLC (% Area) | | |
|---|---|---|---|---|---|---|
| | | | | Before Exposure | After Exposure | Change |
| 9 (coated) | Aluminum Laminate Bag | BHT (0.1) | 7 | 0.2 | 0.5 | 0.3 |
| 9 (uncoated) | Aluminum Laminate Bag | BHT (0.1) | 7 | 0.3 | 0.5 | 0.2 |

A significant reduction in the degradation rate of tablets stored in blister packs and HDPE bottles was observed when 0.2 wt. percent antioxidant was included in the formulation (compare the results for Formulations 5 and 6). BHT (alone) and mixtures of BHT and PG were more effective at inhibiting degradation than SA, but all three antioxidants provide an inhibiting effect relative to untreated azithromycin.

Example 5

Azithromycin Tablet Prepared By Dry Granulation—Slugging

The stability of dry granulated tablet formulations of azithromycin that were pre-compressed by slugging was also assessed with and without adding a food grade antioxidant to the formulation.

Formulations

Formulation 10 [T 582-08]

Formulation 10 was prepared using the same inactive ingredients as Formulation 5.

1. Part I materials were blended in a polyethylene bag and passed through an oscillating granulator (Frewitt®) equipped with a 1 mm aperture screen into a twin shelled Y-cone dry blender.
2. Part II materials were added to the Y-cone blender and mixed.
3. The mix was slugged into slugs using a Manesty B3B tablet press.
4. The slugs were milled in the granulator, which was equipped with a #16 mesh screen and passed into the Y-cone blender.
5. The Part II materials were added to the Y-cone blender and mixed.
6. Oval tablets 9×19 mm were pressed from the mixture on a Manesty B3B rotary tablet press.
7. A portion of the compressed tablets were coated with Opadry® II White. Coating was performed by top spraying a suspension of Opadry II® White in a Fluidized Bed (Uniglatt®). The inlet temperature was 60° C.; the outlet temperature was 40° C. Formulation 10 did not contain an antioxidant.

Formulation 11 [T 582-09]

Formulation 11 used the same inactive ingredients as Formulation 6 and was processed as per Formulation 10. Formulation 11 contained 0.1 wt. % BHT and 0.1 wt. % Propyl Gallate.

Methodology

Stabilized and unstabilized azithromycin tablets prepared by dry granulation with slugging were stored at 60° C. in sealed amber glass bottles for 114 h. Another bottle of stabilized azithromycin tablets was stored "open cap" under identical conditions. Stabilized azithromycin tablets were also studied at 55° C. in polypropylene (PP) and amber glass bottles.

Results

The results of the accelerated stability study on tablets formulated by dry granulation with pre-compression by slugging are recorded in Table 7.

TABLE 7

Comparison of Degradation of Dry-Granulated Azithromycin Tablets with
And Without 0.1 Wt. % BHT and 0.1 Wt. % PG at Elevated Temperatures

| Formulation | Storage Container | Storage Condition | | Total Impurities Detected by HPLC (% Area) | | |
|---|---|---|---|---|---|---|
| | | Temp. (° C.) | Time (h) | Before Exposure | After Exposure | Change |
| 10 (unstabilized) | Amber glass bottle (closed cap) | 60 | 114 | 0.66 | 3.86 | 3.20 |
| 11 | Amber glass bottle (open cap) | 60 | 114 | 0.48 | 1.85 | 1.37 |
| 11 | Amber glass bottle (closed cap) | 60 | 114 | 0.48 | 1.44 | 0.96 |
| 11 | PP bottle (closed cap with small headspace)[1] | 55 | 5 | 0.42 | 0.55 | 0.13 |
| 11 | PP bottle (closed cap with large headspace)[2] | 55 | 5 | 0.42 | 1.16 | 0.74 |
| 11 | amber glass bottle (closed cap with small headspace)[1] | 55 | 5 | 0.42 | 0.49 | 0.07 |

[1]The bottle was filled with tablets.
[2]Two Tablets were added per bottle.

The results recorded in Table 7 show that including 0.1 wt. % BHT and 0.1 wt. % PG in the formulation was effective at inhibiting degradation of azithromycin tablets prepared by dry granulation with slugging. The stabilized tablets showed a three fold reduction in degradation compared to unstabilized tablets at 60° C. under identical closed capped conditions. Even under open cap conditions, the stabilized tablets underwent less than half the degradation than unstabilized tablets stored in a sealed bottled.

Example 6

Powder Suitable for Preparing a Liquid Suspension Dosage Form

The stability of powder formulations suitable for making liquid dosage forms like suspensions, syrups and elixirs also was assessed with and without adding a food grade antioxidant to the formulation.

Formulations

Azithromycin was formulated into a powder that can be constituted as a liquid oral dosage form following the stepwise procedure below using the excipients in Table 8.

TABLE 8

| Stage | Ingredients | Formulation 12 (mg per dose) | Formulation 13 (mg per dose) |
|---|---|---|---|
| Part I | Azithromycin | 210.12* | 210.12* |
|  | Aerosil 200 | 20.00 | 20.00 |
|  | BHT | — | 0.40 |
| Part II | Xanthan Gum | 6.50 | 6.50 |
|  | Klucel LF | 5.00 | 5.00 |
|  | Sodium Phosphate Tribasic | 20.00 | 20.00 |

TABLE 8-continued

| Stage | Ingredients | Formulation 12 (mg per dose) | Formulation 13 (mg per dose) |
|---|---|---|---|
| Part III | Sucrose | 3850.00 | 3850.00 |
|  | Theoretical End Weight | 4111.60 | 4112.00 |

*210.12 mg Azithromycin is equivalent to 200 mg Azithromycin base, based on the specific API batch potency.

Formulation 12 [K-28527]
1 Part I materials were passed through an 18 mesh screen and blended in a Y cone blender.
2. Part II materials were added to the Y-cone blender and mixed.
3. Sucrose (milled 0.8 mm screen) was added to the Y-cone blender and mixed.
4. The blend was passed through Frewitt 0.8 mm screen and blended for 5 minutes. Formulation 12 did not contain an antioxidant.

Formulation 13 [K-28528]
Formulation 13 was prepared using the same inactive ingredients and processing as Formulation 12, except that 0.01 wt. % BHT was added in Step 1.

Methodology

The stability of the powder blend was studied by placing the powder in open capped amber bottles and storing them in a vented over for seven days. The powder also was constituted at 40 mg/ml in water in amber bottles. The bottles were capped and stored at room temperature for seven days.

Results.

The results of the accelerated stability study on the dry powder and the (unaccelerated) stability study on the solution are recorded in Table 9.

TABLE 9

Comparison of Degradation of Azithromycin Powder Formulation for Preparing Liquid Dosage Forms with And Without 0.01 Wt. % BHT

| Formulation | Antioxidants (Wt. %) | Time (days) | T (° C.) | RRT 0.28 (%) | RRT 0.36 (%) | RRT 0.38 (%) | RRT 0.83 (%) | Total Impurity (%) |
|---|---|---|---|---|---|---|---|---|
| 12 | — | 0 | — | 0.15 | 0.24 | 0.11 | <0.1 | 0.50 |
| 12 (dry powder) | — | 7 | 55 | 0.42 | 0.65 | 0.28 | 0.31 | 1.66 |
| % Change |  |  |  | 0.27 | 0.41 | 0.17 | 0.31 | 1.16 |
| 12 (Constituted) | — | 7 | RT | 0.10 | 0.19 | <0.1 | <0.1 | 0.50 |
| % Change[a] |  |  |  | ~0[a] | ~0[a] | ~0[a] | ~0[a] | ~0[a] |
| 13 | — | 0 | — | 0.10 | 0.19 | <0.1 | <0.1 | 0.29 |
| 13 (dry powder) | BHT (0.01) | 7 | 55 | 0.34 | 0.55 | 0.23 | 0.33 | 1.45 |
| % Change |  |  |  | 0.24 | 0.36 | 0.23 | 0.33 | 1.16 |
| 13 (Constituted) | BHT (0.01) | 7 | RT | 0.12 | 0.20 | <0.1 | <0.1 | 0.3 |
| % Change |  |  |  | 0.02 | 0.01 | 0.00 | 0.00 | 0.03 |

[a]The impurity (identified by RRT in the above table) percentage values at 0 days and after 7 days (reconstituted) were of negligible difference, indicating that essentially no degradation occurred during storage of the reconstituted formulation for 7 days.

The data shows that the addition of 0.01 wt. % BHT to the powder formulation for making liquid dosage forms did not improve the stability of azithromycin in the powder when held at 55° C. for seven days. The results of Examples 12 and 13 show that, in general, no additional stability is achieved when the antioxidant is combined with the azithromycin by simple powder mixing of the two, in contrast to forming an intimate admixture of the azithromycin and antioxidant by, e.g., co-precipitation or co-milling as described hereinabove.

What is claimed is:

1. A stabilized azithromycin composition comprising a solid intimate admixture of azithromycin and a stabilizing-effective amount of an antioxidant.

2. The azithromycin composition according to claim 1, wherein less than about 3.5% of the azithromycin is degraded on exposure to 55° C. for seven days.

3. The azithromycin composition according to claim 1, wherein less than about 1.25% of the azithromycin is degraded on exposure to 50° C. for 20 hours.

4. The azithromycin composition according to claim 1, wherein the intimate admixture is achieved by coprecipitation of the azithromycin and the antioxidant.

5. The azithromycin composition according to claim 1, wherein the intimate admixture is achieved by co-milling the azithromycin and the antioxidant.

6. The azithromycin composition according to claim 1, wherein the intimate admixture is achieved by compaction or slugging of the azithromycin and the antioxidant.

7. The azithromycin composition according to claim 1, wherein the azithromycin is azithromycin ethanolate monohydrate.

8. The azithromycin composition according to claim 1, wherein the antioxidant is selected from the group consisting of butylated hydroxyanisole, butylated hydroxytoluene, propyl gallate, ascorbic acid, a pharmaceutically acceptable salt or ester thereof, and mixtures thereof.

9. The azithromycin composition according to claim 1, wherein the antioxidant is present in amount of from about 0.01% to about 10% by weight azithromycin.

10. The azithromycin composition according to claim 1, wherein the antioxidant is present in an amount of from about 0.1% to about 5% by weight azithromycin.

11. The azithromycin composition according to claim 1, wherein the antioxidant is butylated hydroxytoluene.

12. The azithromycin composition according to claim 1, wherein the antioxidant is sodium ascorbate.

13. A pharmaceutical formulation comprising the stabilized azithromycin composition of claim 1 and a carrier, wherein the pharmaceutical formulation is in a form selected from the group consisting of a tablet, granulate, dragee, capsule, powder, solution, emulsion and suspension.

14. The pharmaceutical formulation according to claim 13, wherein the formulation is in a form of a tablet or capsule.

15. The pharmaceutical formulation according to claim 14, wherein the formulation is in the form of a tablet.

16. The pharmaceutical formulation according to claim 13, wherein the antioxidant is selected from the group consisting of butylated hydroxyanisole, butylated hydroxytoluene, propyl gallate, ascorbic acid, a pharmaceutically acceptable salt or ester of one of these compounds, and mixtures thereof.

17. The pharmaceutical formulation according to claim 16, wherein the antioxidant is butylated hydroxytoluene.

18. The pharmaceutical formulation according to claim 16, wherein the antioxidant is present in an amount of from about 0.01% to about 10% by weight azithromycin.

19. The pharmaceutical formulation according to claim 16, wherein the antioxidant is present in an amount of from about 0.1% to about 5% by weight azithromycin.

20. The pharmaceutical formulation according to claim 13, wherein the stabilized azithromycin composition is made by dissolving azithromycin and an antioxidant in a solvent followed by evaporation of the solvent.

21. The pharmaceutical formulation according to claim 20, wherein the azithromycin is azithromycin ethanolate monohydrate.

22. A method for preparing a stabilized azithromycin composition comprising:
dissolving azithromycin and a stabilizing-effective amount of an antioxidant in a solvent; and
co-precipitating azithromycin and antioxidant from said solvent to form a stabilized azithromycin composition.

23. The method of claim 22, further comprising recovering said stabilized azithromycin composition from said solvent.

24. The method according to claim 22, wherein the antioxidant is selected from the group consisting of butylated hydroxyanisole, butylated hydroxytoluene, propyl gallate, ascorbic acid, a pharmaceutically acceptable salt or ester of one of these compounds, and mixtures thereof, and wherein the antioxidant is present in an amount in the range of from about 0.5% to about 10% moles per mole of azithromycin.

25. The method according to claim 24, wherein the antioxidant is butylated hydroxytoluene.

26. A method of preparing a stabilized azithromycin composition comprising:
dissolving azithromycin and a stabilizing-effective amount of an antioxidant in a first solvent to form a mixture; drying the mixture; redissolving the mixture in a second solvent; co-precipitating azithromycin and antioxidant from said solvent to form a stabilized azithromycin composition comprising an intimate admixture of azithromycin and antioxidant.

27. The method of claim 26, further comprising recovering said stabilized azithromycin composition from said solvent.

28. A method of preparing a pharmaceutical formulation comprising granulating a stabilized azithromycin composition comprising an intimate admixture of azithromycin and a stabilizing effective amount of an antioxidant to form granules, followed by shaping said granules into a tablet.

29. The method of claim 28, wherein said granulating comprises wet granulation.

30. The method of claim 28, wherein said granulating comprises dry granulation.

31. The method of claim 30, wherein said dry granulation comprises roller compaction.

32. The method of claim 31, wherein said dry granulation comprises slugging.

33. The method according to claim 28, further comprising coating the tablets.

34. The method of claim 33, wherein the tablets are coated with a coating comprising hydroxypropyl cellulose.

35. A method of treating a bacterial infection in a human or non-human animal in need of such treatment comprising administering to said human or non-human animal a pharmaceutical formulation comprising a stabilized azithromycin composition wherein said composition comprises a solid intimate admixture of azithromycin and a stabilizing-effective amount of an antioxidant.

36. A stabilized azithromycin composition comprising an intimate admixture of azithromycin ethanolate monohydrate and a stabilizing-effective amount of an antioxidant.

37. The azithromycin composition according to claim 36, wherein less than about 3.5% of the azithromycin is degraded on exposure to 55° C. for seven days.

38. The azithromycin composition according to claim 36, wherein less than about 1.25% of the azithromycin is degraded on exposure to 50° C. for 20 hours.

39. The azithromycin composition according to claim 36, wherein the intimate admixture is achieved by coprecipitation of the azithromycin and the antioxidant.

40. The azithromycin composition according to claim 36, wherein the intimate admixture is achieved by co-milling the azithromycin and the antioxidant.

41. The azithromycin composition according to claim 36, wherein the intimate admixture is achieved by compaction or slugging of the azithromycin and the antioxidant.

42. The azithromycin composition according to claim 36, wherein the antioxidant is selected from the group consisting of butylated hydroxyanisole, butylated hydroxytoluene, propyl gallate, ascorbic acid, a pharmaceutically acceptable salt or ester thereof, and mixtures thereof.

43. The azithromycin composition according to claim 36, wherein the antioxidant is present in amount of from about 0.01% to about 10% by weight azithromycin.

44. The azithromycin composition according to claim 36, wherein the antioxidant is present in an amount of from about 0.1% to about 5% by weight azithromycin.

45. The azithromycin composition according to claim 36, wherein the antioxidant is butylated hydroxytoluene.

46. The azithromycin composition according to claim 36, wherein the antioxidant is sodium ascorbate.

47. A pharmaceutical formulation comprising the stabilized azithromycin composition of claim 36 and a carrier, wherein the pharmaceutical formulation is in a form selected from the group consisting of a tablet, granulate, dragee, capsule, powder, solution, emulsion and suspension.

48. The pharmaceutical formulation according to claim 47, wherein the formulation is in a form of a tablet or capsule.

49. The pharmaceutical formulation according to claim 48, wherein the formulation is in the form of a tablet.

50. The pharmaceutical formulation according to claim 47, wherein the antioxidant is selected from the group consisting of butylated hydroxyanisole, butylated hydroxytoluene, propyl gallate, ascorbic acid, a pharmaceutically acceptable salt or ester of one of these compounds, and mixtures thereof.

51. The pharmaceutical formulation according to claim 50, wherein the antioxidant is butylated hydroxytoluene.

52. The pharmaceutical formulation according to claim 50, wherein the antioxidant is present in an amount of from about 0.01% to about 10% by weight azithromycin.

53. The pharmaceutical formulation according to claim 50, wherein the antioxidant is present in an amount of from about 0.1% to about 5% by weight azithromycin.

54. The pharmaceutical formulation according to claim 47, wherein the stabilized azithromycin composition is made by dissolving azithromycin and an antioxidant in a solvent followed by evaporation of the solvent.

55. The pharmaceutical formulation according to claim 54, wherein the azithromycin is azithromycin ethanolate monohydrate.

56. A method of treating a bacterial infection in a human or non-human animal in need of such treatment comprising administering to said human or non-human animal a pharmaceutical formulation comprising a stabilized azithromycin composition wherein said composition comprises an intimate admixture of azithromycin ethanolate monohydrate and a stabilizing-effective amount of an antioxidant.

57. The method of claim 22, wherein said azithromycin comprises azithromycin ethanolate monohydrate.

58. The method of claim 26, wherein said azithromycin comprises azithromycin ethanolate monohydrate.

59. The method of claim 35, wherein said azithromycin comprises azithromycin ethanolate monohydrate.

* * * * *